(12) United States Patent
Richmann

(10) Patent No.: US 8,562,578 B2
(45) Date of Patent: Oct. 22, 2013

(54) DRAINABLE POUCH

(75) Inventor: Sussie Richmann, Hellebaek (DK)

(73) Assignee: Hollister Incorporated, Libertyville, IL (US)

( * ) Notice: Subject to any disclaimer, the term of this patent is extended or adjusted under 35 U.S.C. 154(b) by 191 days.

(21) Appl. No.: 13/057,870

(22) PCT Filed: Jun. 18, 2009

(86) PCT No.: PCT/US2009/047826
§ 371 (c)(1),
(2), (4) Date: Mar. 22, 2011

(87) PCT Pub. No.: WO2010/019313
PCT Pub. Date: Feb. 18, 2010

(65) Prior Publication Data
US 2011/0172618 A1     Jul. 14, 2011

Related U.S. Application Data

(60) Provisional application No. 61/088,833, filed on Aug. 14, 2008.

(51) Int. Cl.
*A61F 5/44*     (2006.01)
(52) U.S. Cl.
USPC .......................................................... 604/335
(58) Field of Classification Search
USPC ......................................................... 604/335
See application file for complete search history.

(56) References Cited

U.S. PATENT DOCUMENTS

| 3,734,154 | A | * | 5/1973 | Polk ................................. 383/57 |
| 3,888,236 | A | * | 6/1975 | Marx ............................. 600/580 |
| 4,084,590 | A | * | 4/1978 | Caraway et al. .............. 604/335 |
| 4,188,989 | A | * | 2/1980 | Andersen ................... 73/864.51 |
| 4,449,971 | A |   | 5/1984 | Cawood |
| 4,462,510 | A | * | 7/1984 | Steer et al. ...................... 222/48 |
| 4,723,944 | A | * | 2/1988 | Jensen .......................... 604/323 |
| D337,382  | S | * | 7/1993 | Wallace ...................... D24/117 |
| 6,045,542 | A |   | 4/2000 | Cawood |
| 6,736,803 | B2 | * | 5/2004 | Cawood ........................ 604/327 |

FOREIGN PATENT DOCUMENTS

WO    WO-01/21115 A1    3/2001
WO    WO-03/086249 A2   10/2003

OTHER PUBLICATIONS

International Search Report for Application No. PCT/US2009/047826, dated Oct. 9, 2009.

* cited by examiner

*Primary Examiner* — Tatyana Zalukaeva
*Assistant Examiner* — Ginger T Chapman
(74) *Attorney, Agent, or Firm* — Levenfeld Pearlstein, LLC

(57) ABSTRACT

A drainable pouch is disclosed which comprises a pair of sidewalls of flexible sheet material having side edges joined together to define a cavity having a discharge end provided with an outlet valve for draining the cavity. The sidewalls also are joined together throughout a central region thereof such that the cavity formed by the sidewalls completely surrounds the central region. With this construction, the central region defines a peripheral edge and has at least one opening in a location which is spaced inwardly of the peripheral edge to receive and secure the outlet valve when the discharge end has been folded.

17 Claims, 13 Drawing Sheets

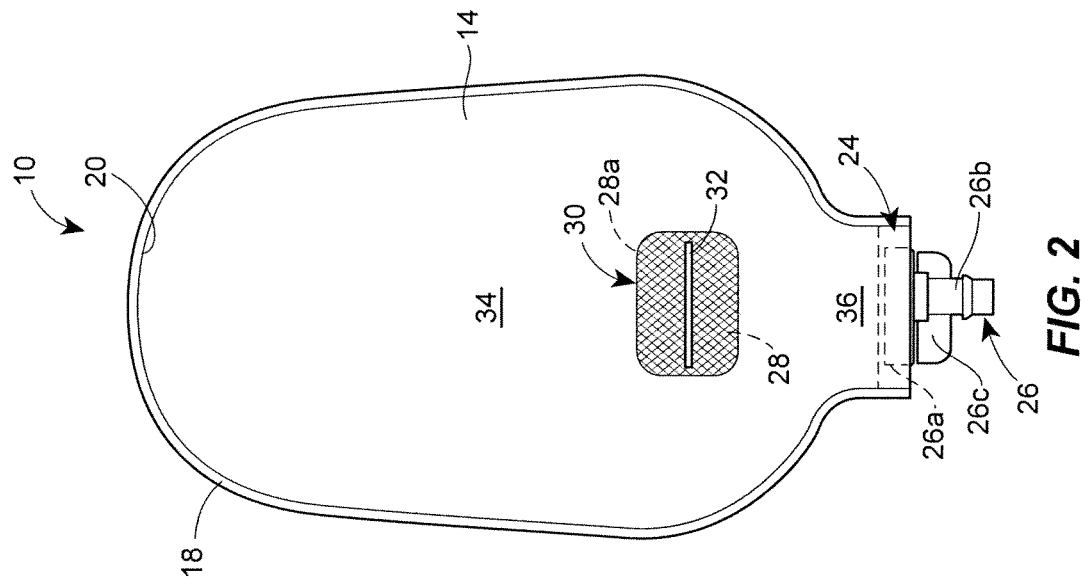
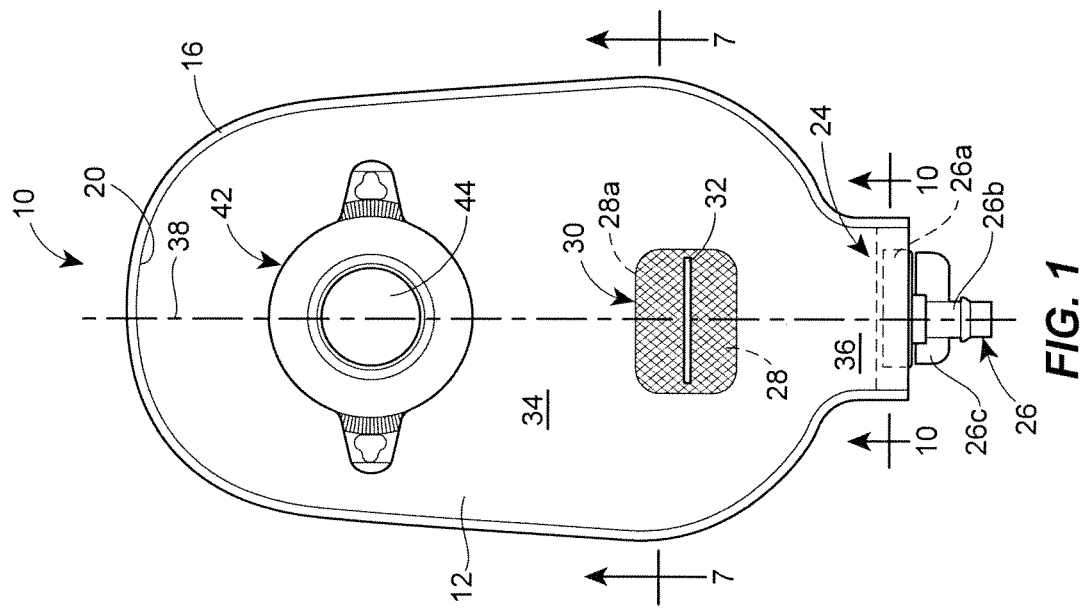

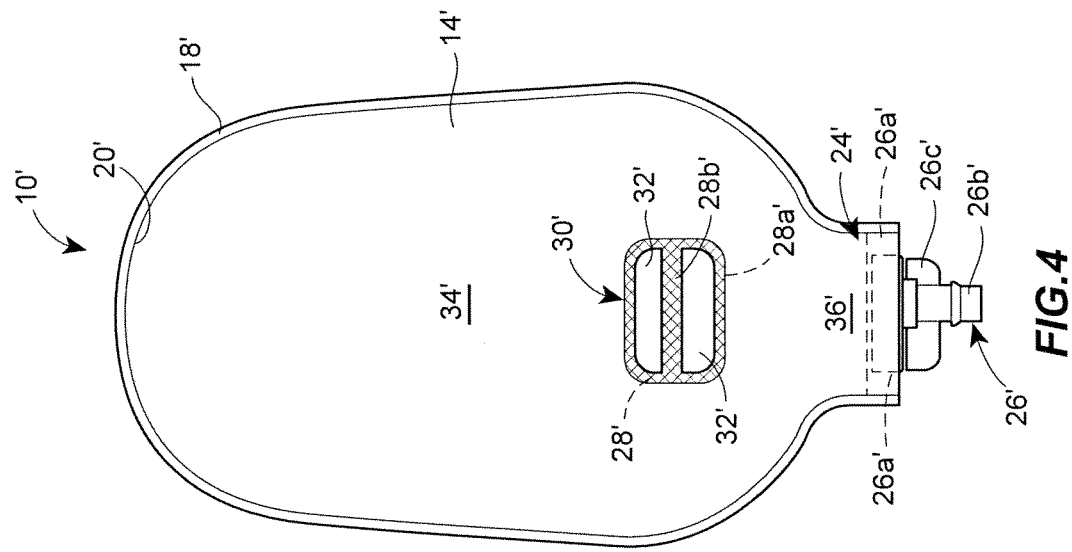
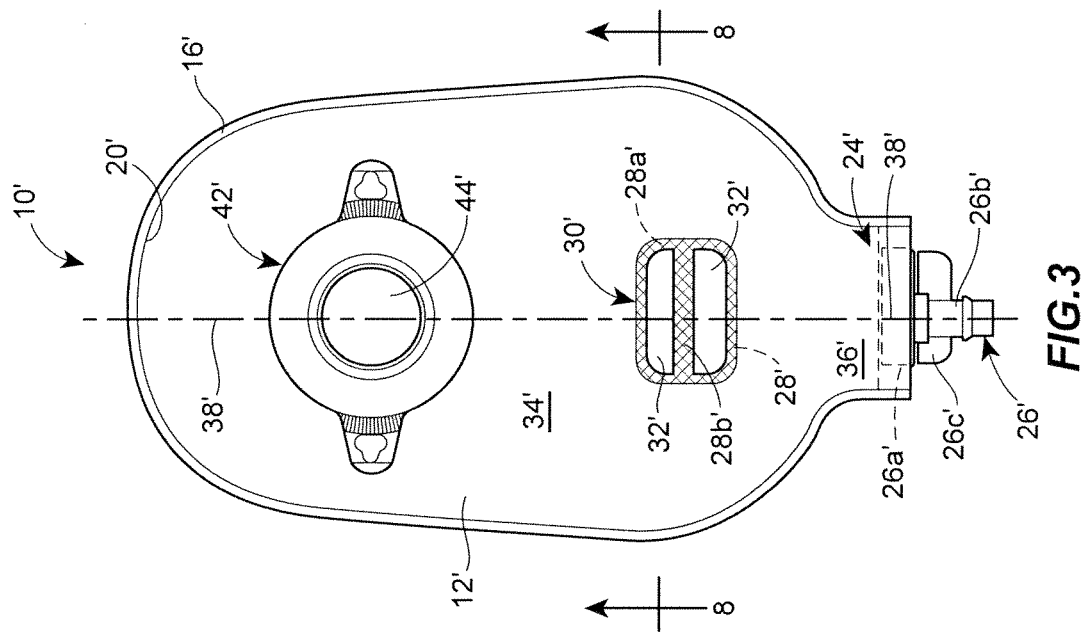

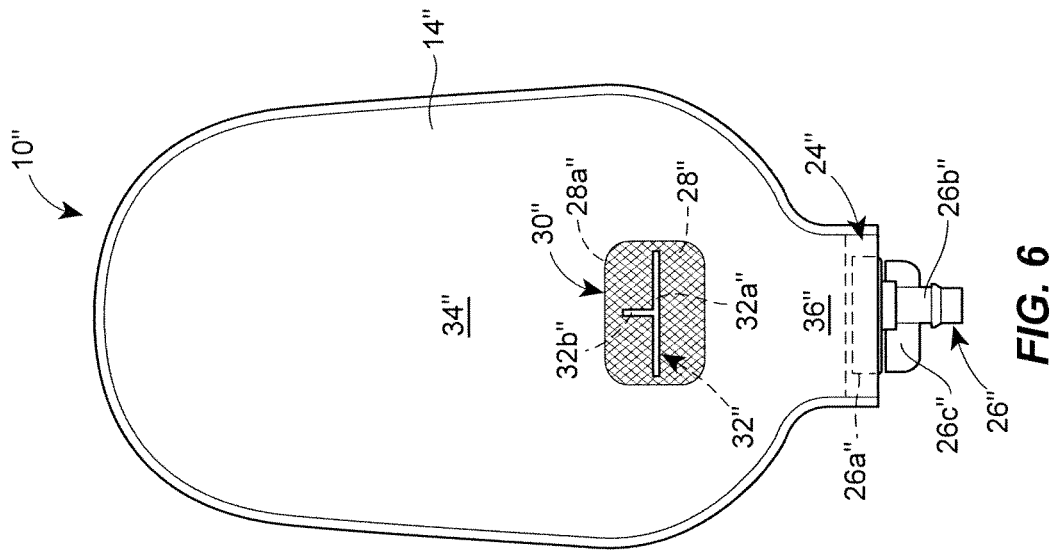
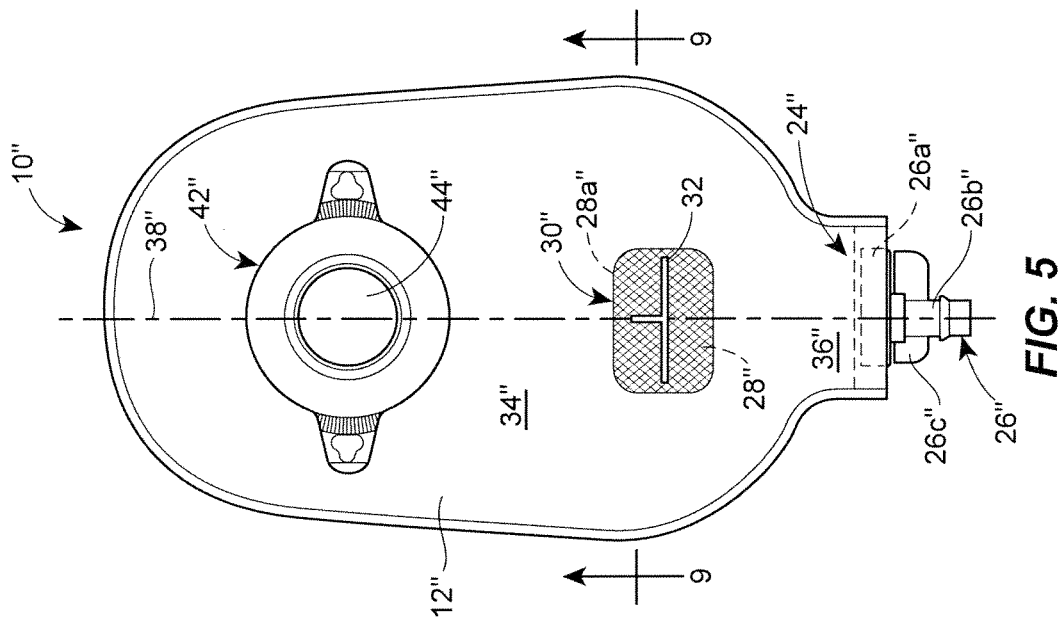

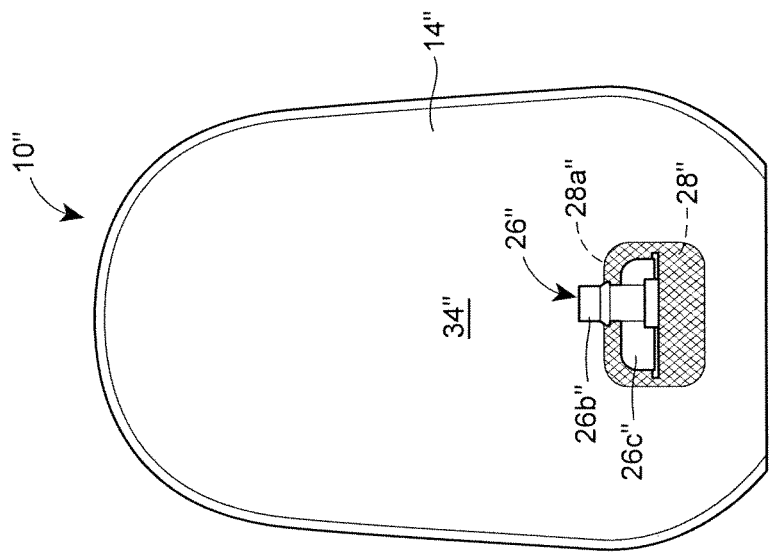
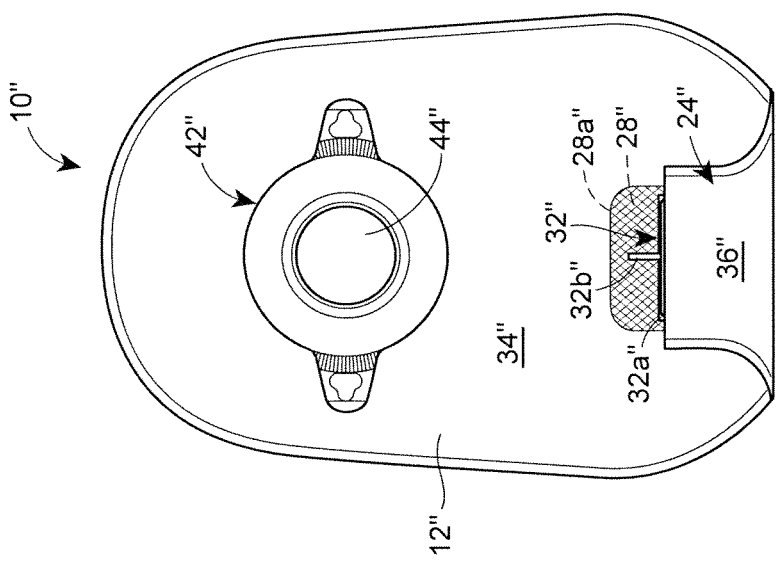

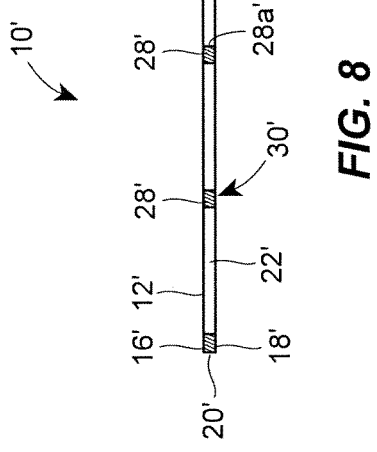
FIG. 7
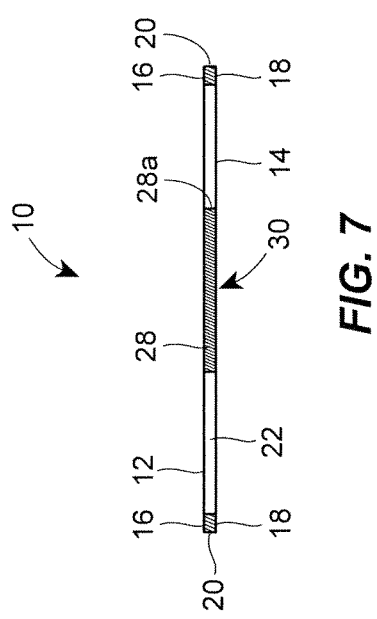
FIG. 8
FIG. 9
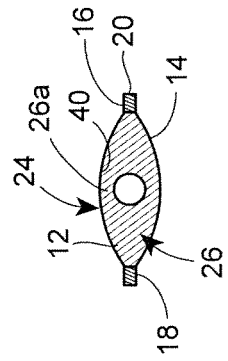
FIG. 10

DRAINABLE POUCH

FIELD OF THE DISCLOSURE

The present disclosure is directed to a pouch for the collection of a liquid or semisolid body waste material and, more particularly, to a drainable pouch that can be closed during collection of liquid or semisolid body waste material and later opened and drained.

BACKGROUND OF THE DISCLOSURE

Drainable pouches for the collection of liquid or semisolid body waste material are well known and typically include flat, opposing sidewalls secured together along their edges to define a collection cavity. One of the sidewalls is provided with an opening to receive a stoma, and means such as a connecting flange is provided for securing the pouch to an adhesive barrier placed to surround the stoma of a patient so that body waste material that is discharged from the stoma will be received within the cavity. At its lower end, the drainable pouch typically has a discharge opening which may be closed during collection of the liquid or semisolid body waste material that passes through the stoma but may be opened for draining the body waste material from the pouch. As will be appreciated, the drainable pouch will typically be provided with a closure for the discharge opening that may take a number of different forms so long as it serves to prevent leakage of the body waste material.

A drainable pouch is typically reusable following periodic emptying of the body waste material, but it is important the pouch be provided with effective sealing in order to avoid odors or contents emanating or leaking from the resealed pouch. This requirement is coupled with a need for the pouch to be easily and conveniently drainable, either directly through the discharge opening, or by reason of connecting an ancillary drainage device in a secure manner to the discharge opening of the pouch. Users of drainable pouches often encounter difficulty and discomfort in unsealing, emptying, and resealing the pouches because of the nature of the drainage systems and manipulations which require greater dexterity than many patients possess.

In addition, drainable pouches often show bulkiness after a period of time of accumulating body waste material. This is true with respect to both liquid and semisolid body waste material because the normally flat sidewalls of such pouches are formed of a thin film which easily expands outwardly as the body waste material accumulates. Further, these pouches often include a rigid outlet valve associated with the discharge opening of the drainable pouch.

These rigid outlet valves are typically sealed within the discharge opening and include a tubular fitting for connection to a collection device. However, such outlet valves can cause significant discomfort or pain when they come into contact with the skin of an individual using such a drainable pouch. Thus, there has been a need to address the apparently unrelated problems of bulking of the drainable pouch and protecting the user from the rigid outlet valve.

SUMMARY OF THE DISCLOSURE

The present disclosure is directed to a drainable pouch comprised of a pair of sidewalls of flexible sheet material having side edges joined together to define a cavity having a discharge end provided with an outlet valve for draining the cavity. The sidewalls also are joined together throughout a central region thereof such that the cavity formed by the sidewalls completely surrounds the central region. With this construction, the central region defines a peripheral edge and has at least one opening in a location which is spaced inwardly of the peripheral edge to receive the outlet valve when the discharge end is folded.

In an exemplary embodiment, the pair of sidewalls of flexible sheet material preferably defines a body portion forming the cavity. Advantageously, the discharge end of the cavity comprises a tubular neck portion integrally formed with and extending from the body portion, and the discharge end is foldable generally along or parallel to a longitudinal axis toward one of the sidewalls to thereby overlap the body portion. After folding the discharge end, the outlet valve will be generally adjacent the opening in the central region so the outlet valve can be received therein.

In one embodiment, the side edges and central region are welded and the at least one opening in the central region includes a slit extending through the sidewalls generally perpendicular to the longitudinal axis of the body portion. In another embodiment, the side edges and central region are welded and the at least one opening in the central region includes a pair of holes forming a strip for receiving and securing the outlet valve after the discharge end is folded.

With the drainable pouch of the present disclosure, the tubular neck portion comprising the discharge end of the cavity defines an opening for receiving the outlet valve. Further, the outlet valve may be formed of a rigid material sealed within the opening for draining the cavity, and it also is preferably formed to include a first portion sealed within the opening and a second tubular portion or fitting which projects therefrom and can be connected to a collection device. In addition, the first portion of the outlet valve may have a generally elongated cross-section and the second tubular portion of the outlet valve may have a generally circular cross-section.

Other advantages and features of the present disclosure will become apparent from the following specification taken in conjunction with the accompanying drawings.

BRIEF DESCRIPTION OF THE DRAWINGS

FIG. 1 is a front elevational view of a first embodiment of a drainable pouch according to the present disclosure;

FIG. 2 is a rear elevational view of the first embodiment of drainable pouch illustrated in FIG. 1;

FIG. 3 is a front elevational view of a second embodiment of drainable pouch according to the present disclosure;

FIG. 4 is a rear elevational view of the second embodiment of drainable pouch illustrated in FIG. 3;

FIG. 7 is a cross-sectional view taken generally along the line 7-7 of FIG. 1 illustrating the sidewall welds of the first embodiment;

FIG. 8 is a cross-sectional view taken generally along the line 8-8 of FIG. 3 illustrating the sidewall welds of the second embodiment;

FIG. 9 is a cross-sectional view taken generally along the line 9-9 of FIG. 5 illustrating the sidewall welds of the third embodiment; and FIG. 10 is a cross-sectional view taken generally along the line 10-10 of FIG. 1 illustrating the outlet valve in the discharge end of the pouch.

DETAILED DISCLOSURE OF THE EXEMPLARY EMBODIMENTS

Figure 2A:
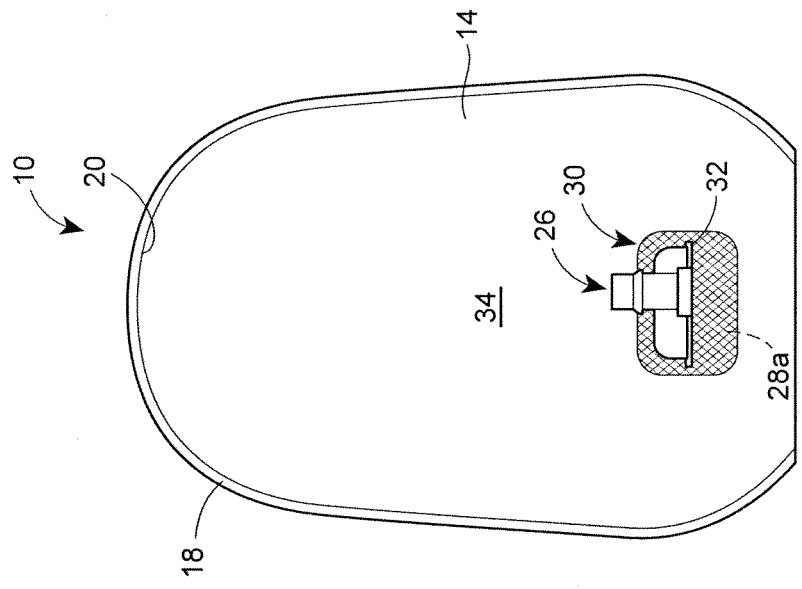
FIG. 2A is a view similar to FIG. 2 but with the outlet valve received within an opening in the drainable pouch.

In the various illustrations given, and with reference first to FIGS. 1 and 2, a first embodiment of a drainable pouch according to the present disclosure is generally designated by the reference numeral 10. The drainable pouch 10 is formed of a pair of sidewalls 12 and 14 of flexible sheet material having side edges 16 and 18 joined together about the perimeter of the pouch as by welding at 20 to define a cavity 22 therebetween (see FIG. 7). Further, the cavity 22 formed by the side walls 12 and 14 has a discharge end as at 24 provided with an outlet valve 26 for draining the cavity 22 of liquid or semisolid body waste materials collected therein.

Figure 1A:
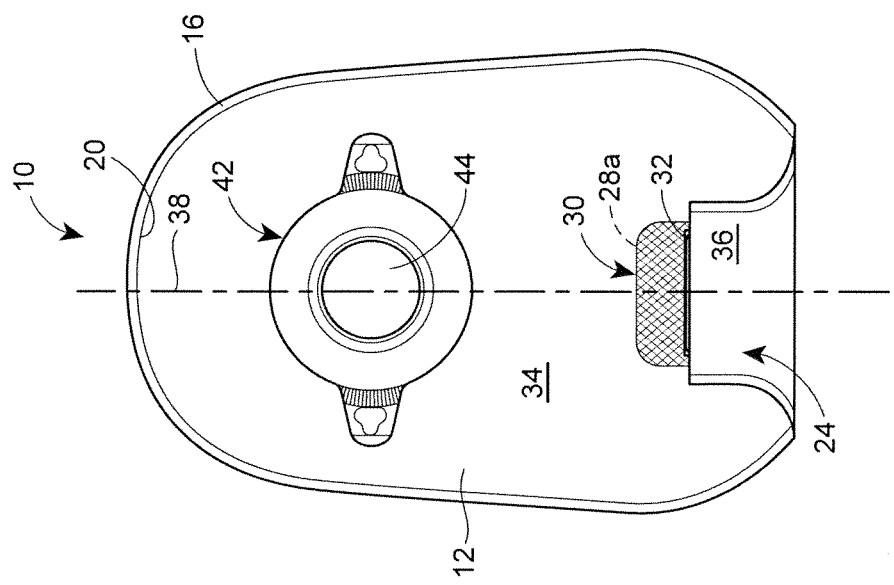
FIG. 1A is a view similar to FIG. 1 but with the outlet valve received within an opening in the drainable pouch.
Figure 1B:
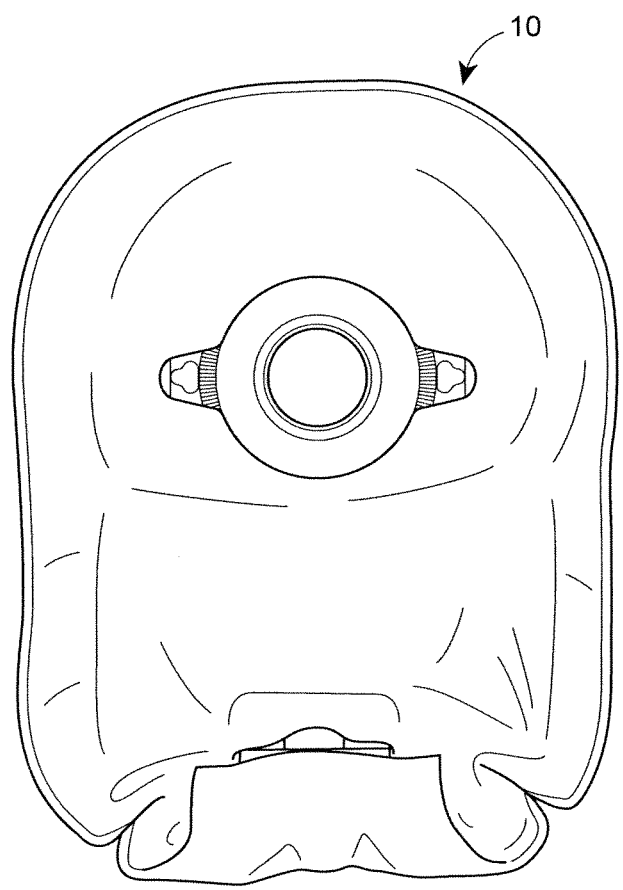
FIG. 1B is a view similar to FIG. 1A but showing the drainable pouch in a substantially filled condition.
Figure 2B:
FIG. 2B is a view similar to FIG. 2A but showing the drainable pouch in a substantially filled condition.

Referring to FIGS. 1, 2 and 7, it will be seen that the sidewalls 12 and 14 are joined together as by welding at 28 throughout a central region 30 thereof such that the cavity 22 formed by the sidewalls 12 and 14 completely surrounds the central region 30 defined by the welding at 28. With this construction, the central region 30 defined by the welding at 28 forms an internal peripheral edge 28a facing the cavity 22, and it also has at least one opening such as the slit or slot 32 in a location inwardly of the internal peripheral edge 28a to receive the outlet valve 26 when the discharge end 24 is folded (see FIGS. 1A and 2A).

As will be appreciated, the pair of sidewalls 12 and 14 of flexible sheet material preferably defines a body portion 34 forming the cavity 22. The discharge end 24 of the cavity 22 may then advantageously comprise a tubular neck portion 36 integrally formed with and extending from the body portion 34. When so formed, the discharge end 24 is foldable generally along or parallel to a longitudinal axis 38 toward one of the sidewalls 12 and 14 to overlap the body portion 34.

After the discharge end 24 has been folded, the outlet valve 26 will be generally adjacent the opening or slit 32 in the central region 30 so the outlet valve 26 can be received and stored therein as shown in FIGS. 1A and 2A. It will be appreciated from the drawings that the outlet valve 26 is located generally along or parallel to the longitudinal axis 38 of the body portion 34, and the slit 32 extends through the sidewalls 12 and 14 generally perpendicular to the longitudinal axis 38 of the body portion 34. Preferably, the outlet valve 26 is formed of a rigid material in contrast to the soft, flexible material of the sidewalls 12 and 14, and is sealed in an opening 40 in the discharge end 24 (see FIG. 10).

Referring to FIGS. 1, 2 and 10, the outlet valve 26 preferably includes a first portion 26a sealed within the opening 40 in the discharge end 24 and a second tubular portion 26b which may take the form of a barbed fitting. The outlet valve 26 may also include a rotatable flange 26c for opening and closing the valve. With this construction, it will be appreciated that the second tubular portion 26b projects from the first portion 26a such that a flexible tube can be inserted over the barbed fitting to drain the contents of the cavity 22 into a collection device.

As shown in FIG. 10, the first portion 26a of the outlet valve 26 may have a generally elongated cross-section. The generally elongated first portion 26a may then be positioned within the opening 40 and the flexible sheet material at the discharge end 24 of the cavity 22 may be sealed to the generally elongated first portion 26a. Referring to FIGS. 1 and 2, the second tubular portion 26b of the outlet valve 26 may have a generally circular cross-section.

Referring to FIGS. 3 and 4, a second embodiment of a drainable pouch which is similar in many respects to the embodiment of FIGS. 1 and 2 is generally designated by the reference numeral 10'. The drainable pouch 10' is formed of a pair of sidewalls 12' and 14' of flexible sheet material having side edges 16' and 18' joined together about the perimeter of the pouch as by welding at 20' to define a cavity 22' therebetween (see FIG. 8). Further, the cavity 22' formed by the side walls 12' and 14' has a discharge end 24' provided with an outlet valve 26' for draining the cavity 22' of liquid or semi-solid body waste materials.

Figure 4A:
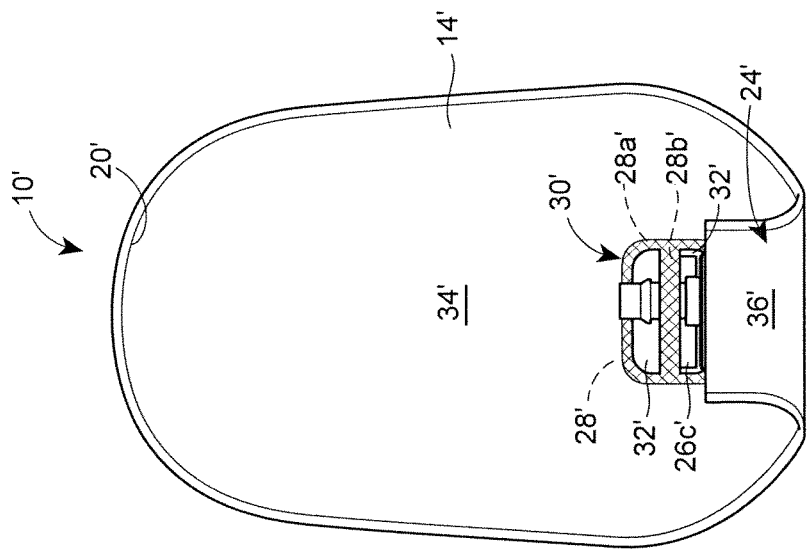
FIG. 4A is a view similar to FIG. 4 but with the outlet valve received within an opening in the drainable pouch.
Figure 3A:
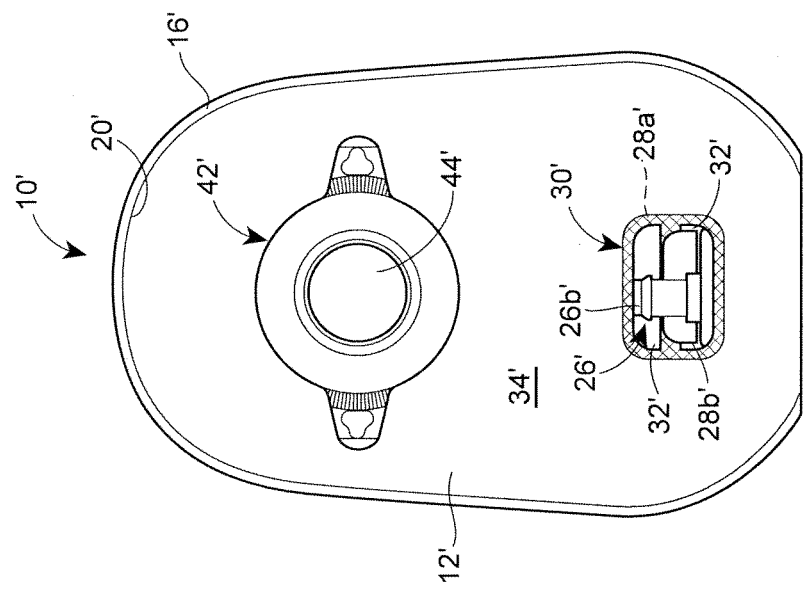
FIG. 3A is a view similar to FIG. 3 but with the outlet valve received within an opening in the drainable pouch.
Figure 3B:
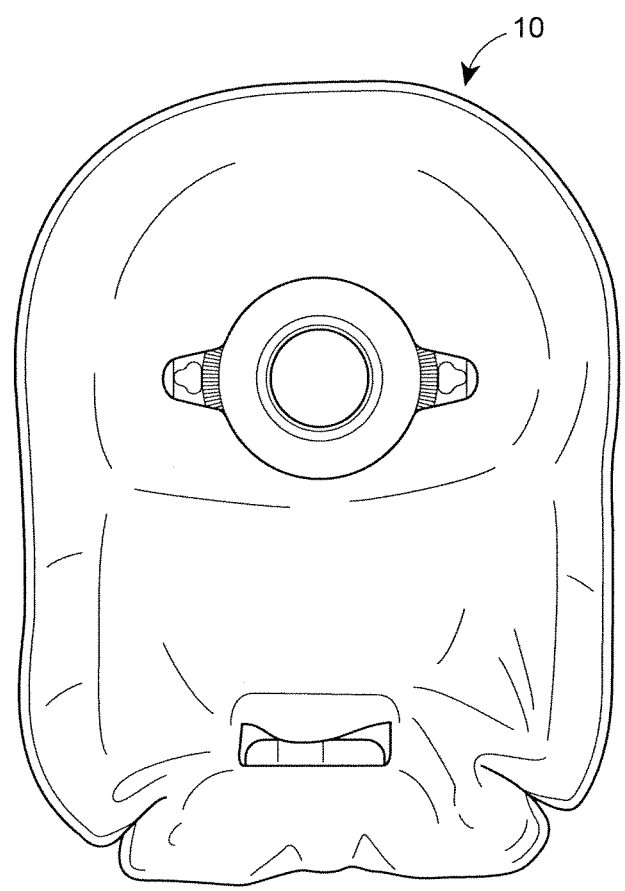
FIG. 3B is a view similar to FIG. 3A but showing the drainable pouch in a substantially filled condition.
Figure 4B:
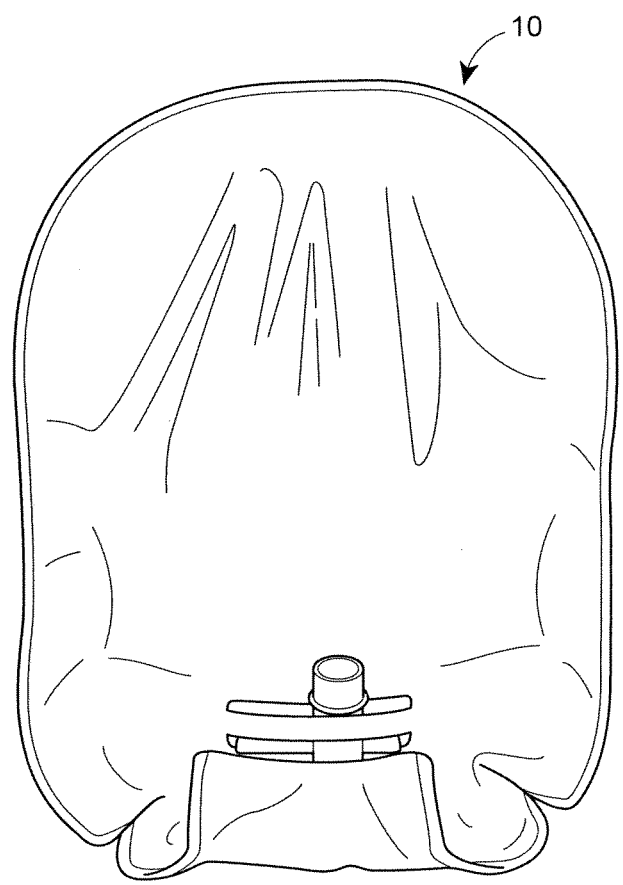
FIG. 4B is a view similar to FIG. 4A but showing the drainable pouch in a substantially filled condition.

Referring to FIGS. 3, 4 and 8, it will be seen that the sidewalls 12' and 14' are joined together as by welding at 28' throughout a central region 30' thereof such that the cavity 22' formed by the sidewalls 12' and 14' completely surrounds the central region 30' defined by the welding at 28'. With this construction, the central region 30' defined by the welding at 28' forms an internal peripheral edge 28a' facing the cavity 22', but it has a pair of openings such as the holes 32' inwardly of the internal peripheral edge 28a' to receive the outlet valve 26' when the discharge end 24' is folded (see FIGS. 3A and 4A).

By forming the pair of holes 32', the welding at 28' results in a central welded strip 28b' between the holes 32' which cooperates with the outlet valve 26' in a manner described in more detail below.

As will be appreciated, the pair of sidewalls 12' and 14' of flexible sheet material preferably defines a body portion 34' forming the cavity 22'. The discharge end 24' of the cavity 22 then advantageously comprises a tubular neck portion 36' integrally formed with and extending from the body portion 34'. When so formed, the discharge end 24' is foldable generally along or parallel to a longitudinal axis 38' toward one of the sidewalls 12' and 14' to overlap the body portion 34'.

After the discharge end 24' has been folded, the outlet valve 26' will be generally adjacent the holes 32' in the central region 30' so the outlet valve 26' can be received and stored therein as shown in FIGS. 3A and 4A. It will be appreciated from the drawings that the outlet valve 26' is located generally along or parallel to the longitudinal axis 38' of the body portion 34', and the holes 32' extend through the sidewalls 12' and 14' generally perpendicular to the longitudinal axis 38' of the body portion 34'. Preferably, the outlet valve 26' is formed of a rigid material in contrast to the soft, flexible material of the sidewalls 12' and 14', and is sealed in an opening such as 40 (FIG. 10) in the discharge end 24'.

As for the embodiment of FIGS. 3 and 4, the outlet valve 26' is preferably identical to the outlet valve 26 illustrated in FIGS. 1, 2 and 10. In particular, it preferably includes a first portion 26a' similar or identical to first portion 26a (FIG. 10) and sealed within an opening such as 40 (FIG. 10) in the discharge end 24' and a second tubular portion 26b' which may take the form of a barbed fitting, and the outlet valve 26' may also advantageously include a rotatable flange 26c' provided for opening and closing the valve. With this construction, it will be appreciated that the second tubular portion 26b' projects from the first portion 26a' such that a flexible tube can be inserted over the barbed fitting to drain the contents of the cavity 22' into a collection device.

The first portion 26a' of the outlet valve 26' may have a generally elongated cross-section which may be positioned within the opening such as 40 (FIG. 10). The flexible sheet material at the discharge end 24' of the cavity 22' may be sealed to the generally elongated first portion 26a'. Further, the second tubular portion 26b' of the outlet valve 26' may have a generally circular cross-section.

Figure 5B:
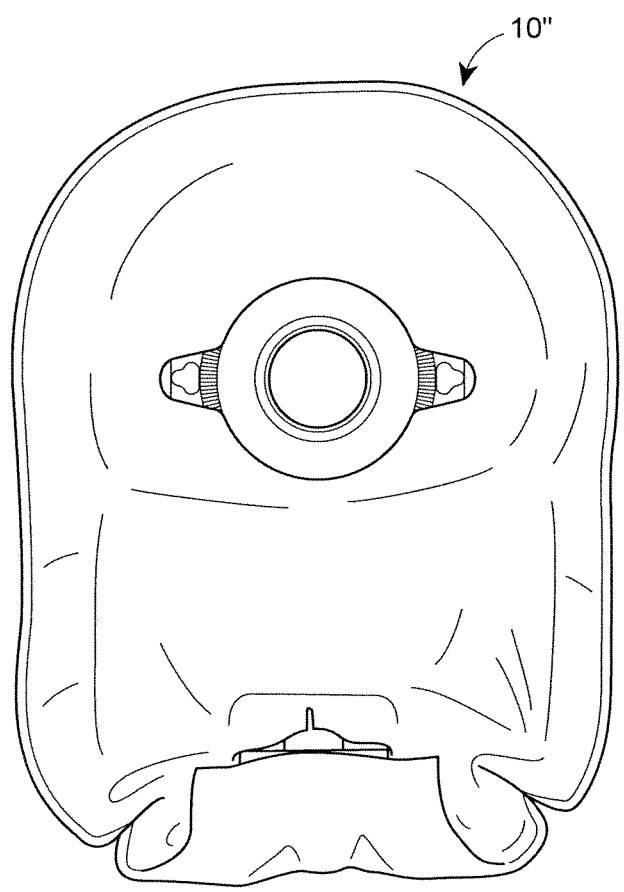
FIG. 5 is a rear elevational view of the third embodiment of drainable pouch according to the present disclosure.
FIG. 5A is a view similar to FIG. 5 but with the outlet valve received within an opening in the drainable pouch.
Figure 6B:
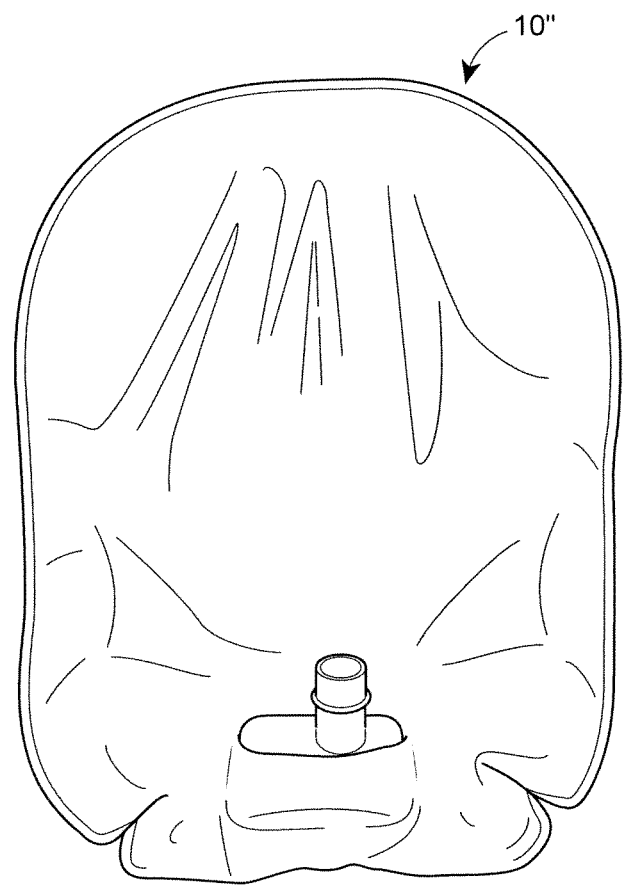
FIG. 6 is a rear elevational view of the third embodiment of drainable pouch illustrated in FIG. 5.
FIG. 6A is a view similar to FIG. 6 but with the outlet valve received within an opening in the trainable pouch.

Referring to FIGS. 5 and 6, a third embodiment of a drainable pouch which is similar in many respects to the embodiment of FIGS. 1 and 2 is generally designated by the reference numeral 10". The drainable pouch 10" is formed of a pair of sidewalls 12" and 14" of flexible sheet material having side edges 16" and 18" joined together about the perimeter of the pouch as by welding at 20" to define a cavity 22" therebetween (see FIG. 9). Further, the cavity 22" formed by the side walls 12" and 14" has a discharge end as at 24" provided with an outlet valve 26" for draining the cavity 22" of liquid or semisolid body waste materials collected therein.

Referring to FIGS. 5, 6 and 9, it will be seen that the sidewalls 12" and 14" are joined together as by welding at 28" throughout a central region 30" thereof such that the cavity 22" formed by the sidewalls 12" and 14" completely surrounds the central region 30" defined by the welding at 28". With this construction, the central region 30" defined by the welding at 28" forms an internal peripheral edge 28a" facing the cavity 22", but it also has at least one opening such as the slit 32" in a location inwardly of the internal peripheral edge 28a" to receive the outlet valve 26" when the discharge end 24" is folded (see FIGS. 5A and 6A).

As will be appreciated, the slit 32" has a first portion 32a" which corresponds to the entire slit 32 in FIG. 1 and it also has a second portion 32b" which is transverse to the first portion, generally along or parallel to the longitudinal axis 38" of the body portion 34", and in alignment with the second tubular portion 26b" of the outlet valve 26" before the discharge end 24" has been folded. With this construction, it will be appreciated that it may be easier for the outlet valve 26" to be received within the slit 32" once the discharge end 24" has been folded than is the case with the slit 32 in FIG. 1 because the second tubular portion 26b" of the outlet valve 26" which has a barbed fitting can more easily be passed through the slit 32" to rest in the positions shown in FIGS. 5A and 6A as a result of the aligned second portion 32b" of the slit 32".

As will be appreciated, the pair of sidewalls 12" and 14" of flexible sheet material preferably defines a body portion 34" forming the cavity 22". The discharge end 24" of the cavity 22" then advantageously comprises a tubular neck portion 36" integrally formed with and extending from the body portion 34". When so formed, the discharge end 24" is foldable generally along or parallel to the longitudinal axis 38" toward one of the sidewalls 12" and 14" to overlap the body portion 34".

After the discharge end 24" has been folded, the outlet valve 26" will be generally adjacent the slit 32" in the central region 30" so the outlet valve 26" can be received and stored therein as shown in FIGS. 5A and 6A. It will be appreciated from the drawings that the outlet valve 26" is located generally along or parallel to the longitudinal axis 38" of the body portion 34", and the slit 32" extends through the sidewalls 12" and 14" as previously described. Preferably, the outlet valve 26" is formed of a rigid material in contrast to the soft, flexible material of the sidewalls 12" and 14", and is sealed in an opening such as 40 (FIG. 10) in the discharge end 24".

As for the embodiment of FIGS. 5 and 6, the outlet valve 26" is preferably identical to the outlet valve 26 illustrated in FIGS. 1, 2 and 10. In particular, it preferably includes a first portion 26a" similar or identical to the first portion 26a (FIG. 10) sealed within the opening such as 40 in the discharge end 24" and a second tubular portion 26b" which may take the form of a barbed fitting, and the outlet valve 26" may also advantageously include a rotatable flange 26c" provided for opening and closing the valve. With this construction, it will be appreciated that the second tubular portion 26b" projects from the first portion 26a" such that a flexible tube can be inserted over the barbed fitting to drain the contents of the cavity 22" into a collection device.

The first portion 26a" of the outlet valve 26" may have a generally elongated cross-section which may be positioned within the opening such as 40. The flexible sheet material at the discharge end 24" of the cavity 22" may be sealed to the generally elongated first portion 26a". Further, the second tubular portion 26b" of the outlet valve 26" may have a generally circular cross-section.

While not important to understanding the features of the present disclosure, it will be appreciated from FIGS. 1, 3 and 5 that the drainable pouches 10, 10' and 10" will suitably be provided with a connecting flange such as 42, 42' and 42". These connecting flanges 42, 42' and 42" are provided for attaching the respective drainable pouches 10, 10' and 10" to the body so that holes 44, 44' and 44" through the respective connecting flanges 42, 42' and 42" are in line with a stoma for drainage of body waste material. More specifically, the drainable pouches 10, 10' and 10" are well suited as urostomy pouches to receive liquid and semisolid body waste material.

For this application, the outlet valves 26, 26' and 26" are typically formed of a rigid material for attachment to a collection device. The rigid material may comprise a suitable plastic, but it can cause considerable discomfort by rubbing against or digging into the skin of a person using one of the drainable pouches 10, 10' and 10". However, the drainable pouches 10, 10' and 10" overcome this problem by providing a way to isolate the outlet valves from the skin.

With the drainable pouch 10 (FIGS. 1 and 2), the discharge end 24 is folded generally along or parallel to the longitudinal axis 38 so as to overlie the sidewall 12. The second tubular portion 26b and the rotatable flange 26c are then inserted through the slit 32 placing them on the side of the drainable pouch 10 opposite to the connecting flange 42. Thus, the portions of the outlet valve 26 externally of the drainable pouch 10 are located on the side of the drainable pouch 10 opposite the connecting flange 42 and opposite the sidewall 12 which is adjacent the skin during use (see FIGS. 1A and 2A).

With the drainable pouch 10' (FIGS. 3 and 4), the discharge end 24' is folded generally along or parallel to the longitudinal axis 38' so as to overlie the sidewall 14'. The second tubular portion 26b' and the rotatable flange 26c' are then inserted through the hole 32 located nearest to the discharge end 24', under the central welded strip 38', and then through the hole 32 located furthest from the discharge end 24'. Thus, the portions of the outlet valve 26' externally of the drainable pouch 10' are generally located in recessed relation relative to the side of the drainable pouch 10' having the connecting flange 42' and are therefore recessed relative to the sidewall 12' which is adjacent the skin during use (see FIGS. 3A and 4A).

With the drainable pouch 10" (FIGS. 5 and 6), the discharge end 24" is folded generally along or parallel to the longitudinal axis 38" so as to overlie the sidewall 12". The second tubular portion 26b" and the rotatable flange 26c" are then inserted through the slit 32" placing them on the side of the drainable pouch 10" opposite to the connecting flange 42". Thus, the portions of the outlet valve 26" externally of the drainable pouch 10" are located on the side of the drainable pouch 10" opposite the connecting flange 42" and opposite the sidewall 12" which is adjacent the skin during use (see FIGS. 5A and 6A).

In addition to the foregoing, it will be appreciated that the central welded regions 30, 30' and 30" serve to prevent the appearance of bulkiness after a period of time of accumulating body waste material. The central welded regions 30, 30' and 30" serve to hold together the normally flat sidewalls 12, 14; 12', 14'; and 12", 14", respectively, which are formed of a thin odor barrier and liquid impervious film. As the cavities 22, 22' and 22" fill with liquid or semisolid body waste material, the sidewalls 12, 14; 12', 14'; and 12", 14" are thereby prevented from expanding outwardly as they would otherwise do as body waste material accumulates. This will be appreciated by referring in particular to FIGS. 1B, 2B, 3B, 4B, 5B, and 6B which are front and rear views illustrating filled drainable pouches 10, 10' and 10", respectively. As a result, the central welded regions 30, 30' and 30" serve to prevent the appearance of bulkiness and to receive and secure the rigid outlet valves 26, 26' and 26" while eliminating discomfort or pain to the user.

As a still additional benefit of the present disclosure, the folding of the discharge ends 24, 24' and 24" makes it possible to make the drainable pouches 10, 10' and 10" larger because they can be folded as described. This makes it possible to initially fold the discharge ends 24, 24' and 24" such that the drainable pouches 10, 10' and 10" have a smaller overall area, and the cavities 22, 22' and 22" have a first, smaller capacity to receive body waste material and, later, to unfold the discharge ends 24, 24' and 24" such that the drainable pouches 10, 10' and 10" have a larger overall area and the cavities 22, 22' and 22" have a second, larger capacity to receive body waste material should the user so desire. While the outlet valves 26, 26' and 26" would be adjacent the skin after unfolding, this may be acceptable to the user in order to lengthen the time before which the body waste material would need to be drained.

While in the foregoing there have been set forth representative embodiments of the present disclosure, it will be appreciated that the details herein given may be varied by those skilled in the art without departing from the true scope and spirit of the appended claims.

What is claimed is:

1. A drainable pouch, comprising: a pair of sidewalls of flexible sheet material having side edges joined together to define a cavity having a discharge end provided with an outlet valve for draining the cavity, the sidewalls also being joined together throughout a central region thereof such that the cavity formed by the sidewalls completely surrounds the central region, the central region defining a peripheral edge and having at least one opening inwardly of the peripheral edge, wherein the at least one opening is configured to receive and secure the outlet valve when the discharge end is folded.

2. The drainable pouch of claim 1 wherein the pair of sidewalls of flexible sheet material defines a body portion forming the cavity and the discharge end of the cavity comprises a tubular neck portion integrally formed with and extending from the body portion.

3. The drainable pouch of claim 1 wherein the discharge end is foldable toward one of the sidewalls to overlap the body portion to bring the outlet valve generally adjacent the central region so the opening, in the central region can receive the outlet valve.

4. The drainable pouch of claim 2 wherein the side edges and central region are joined together by welding and the at least one opening in the central region includes a slit extending through the sidewalls generally perpendicular to a longitudinal axis of the body portion.

5. The drainable pouch of claim 2 wherein the side edges and central region are joined together by welding and the at least one opening in the central region includes a pair of holes forming a strip for receiving and securing the outlet valve after the discharge end is folded.

6. The drainable pouch of claim 2 wherein the tubular neck portion comprising the discharge end of the cavity defines an opening for receiving the outlet valve which is formed of a rigid material and is sealed within the opening for draining the cavity.

7. A drainable pouch, comprising: a pair of sidewalls of flexible sheet material having side edges welded together to define a body portion having a cavity with a discharge end provided with an outlet valve for draining the cavity, the discharge end comprising a tubular neck portion integrally formed with and extending from the body portion and being foldable toward one of the sidewalls to overlap the body portion, the sidewalls also being welded together throughout a central region of the body portion such that the cavity formed by the body portion completely surrounds the central region, and the central region defining an internal peripheral edge confronting the cavity and having at least one opening extending through the welded sidewalls inwardly of the peripheral edge, wherein the at least one opening is configured to receive and secure the outlet valve when the discharge end is folded.

8. The drainable pouch of claim 7 wherein the at least one opening in the central region includes a slit extending through the sidewalls generally perpendicular to a longitudinal axis of the body portion.

9. The drainable pouch of claim 7 wherein the at least one opening in the central region includes a pair of holes forming a strip to receive and secure the outlet valve after the discharge end is folded.

10. The drainable pouch of claim 7 wherein the tubular neck portion defines an opening for receiving the outlet valve, the outlet valve being formed of a rigid material and sealed within the opening.

11. A drainable urostomy pouch, comprising: a pair of sidewalls of flexible sheet material having side edges welded together to define a body portion having a cavity with a discharge end provided with an outlet valve for draining the cavity, the discharge end comprising a tubular neck portion integrally formed with and extending from the body portion and being foldable toward one of the sidewalls to overlap the body portion, the tubular neck portion defines an opening for receiving the outlet valve, the outlet valve being formed of a rigid material and having a first portion sealed within the opening and a second tubular portion projecting therefrom, the sidewalls also being welded together throughout a central region of the body portion such that the cavity formed by the body portion completely surrounds the central region, and the central region defining an internal peripheral edge confronting the cavity and having at least one opening extending through the welded sidewalls inwardly of the peripheral edge, the opening in the central region and the rigid outlet valve lying generally along or parallel to a longitudinal axis of the body portion so the opening can receive and secure the outlet valve when the discharge end is folded to overlap the body portion.

12. The drainable urostomy pouch of claim 11 wherein the at least one opening in the central region includes a slit extending through the sidewalls generally perpendicular to a longitudinal axis of the body portion.

13. The drainable urostomy pouch of claim 11 wherein the at least one opening in the central region includes a pair of holes forming a strip to receive and secure the outlet valve after the discharge end is folded.

14. The drainable urostomy pouch of claim 11 wherein the first portion of the outlet valve has a generally elongated cross-section and the second tubular portion of the outlet valve has a generally circular cross-section.

15. The drainable urostomy pouch of claim 11 wherein the central region is generally rectangular in shape and has a width generally corresponding to the width of the opening defined by the tubular neck portion.

16. The drainable urostomy pouch of claim 13 wherein the central region and the boles forming the strip are generally rectangular to define the central region as a welded perimeter region entirely surrounding the holes.

17. The drainable urostomy pouch of claim 16 wherein the holes have a greater width than the diameter of the tubular portion of the outlet valve so the strip can secure the outlet valve after the discharge end is folded.

\* \* \* \* \*